(12) United States Patent
Da Silva Rodrigues et al.

(10) Patent No.: US 10,799,715 B2
(45) Date of Patent: Oct. 13, 2020

(54) ADAPTIVE RADIATION THERAPY PLANNING

(71) Applicant: KONINKLIJKE PHILIPS N.V., Eindhoven (NL)

(72) Inventors: Pedro Jorge Da Silva Rodrigues, Veldhoven (NL); Alfonso Agatino Isola, Eindhoven (NL); Andreia Maria Araujo Trindade Rodrigues, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 317 days.

(21) Appl. No.: 15/773,386

(22) PCT Filed: Nov. 7, 2016

(86) PCT No.: PCT/EP2016/076764
§ 371 (c)(1),
(2) Date: May 3, 2018

(87) PCT Pub. No.: WO2017/089097
PCT Pub. Date: Jun. 1, 2017

(65) Prior Publication Data
US 2018/0318605 A1 Nov. 8, 2018

(30) Foreign Application Priority Data

Nov. 27, 2015 (EP) ..................................... 15196772

(51) Int. Cl.
*A61N 5/10* (2006.01)
(52) U.S. Cl.
CPC ......... *A61N 5/1038* (2013.01); *A61N 5/1039* (2013.01); *A61N 5/1045* (2013.01); *A61N 5/1049* (2013.01); *A61N 2005/1041* (2013.01)

(58) Field of Classification Search
CPC ........ A61N 5/00; A61N 5/1001; A61N 5/103; A61N 5/1038; A61N 5/1041
USPC ......................................................... 600/1–7
See application file for complete search history.

(56) References Cited

U.S. PATENT DOCUMENTS

| 7,574,251 | B2 | 8/2009 | Lu et al. |
| 8,363,785 | B2 | 1/2013 | Nord |

OTHER PUBLICATIONS

Nawrocki, S. et al., "Clinical study and numerical simulation of brain cancer dynamics under radiotherapy", Commun Nonlinear Sci Numer Simulat 22 (2015) 564-573.
Powathil, G.G. et al., "Towards Predicting the Response of a Solid Tumour to Chemotherapy and Radiotherapy treatments: Clinical Insight from a Computational Model", PLoS Comput Biol 9(7): e1003120, Jul. 2013.
(Continued)

*Primary Examiner* — John P Lacyk (57) ABSTRACT

The invention relates to a system for generating a radiotherapy treatment plan (33; 34) for treating a target structure within a patient body. The system comprises (i) a modeling unit configured to determine a series of estimates (31*a-d*; 32*a-d*) of a delineation of the target structure for consecutive points of time during the radiation therapy treatment on the basis of a model quantifying changes of the delineation with time, and (ii) a planning unit configured to determine the treatment plan (33; 34) on the basis of the series of estimates (31*a-d*; 32*a-d*) of the delineation of the target structure. Further, the invention relates to method carried out in the system.

14 Claims, 3 Drawing Sheets

(56) References Cited

OTHER PUBLICATIONS

Liu, Y et al., "Patient Specific Tumor Growth Prediction Using Multimodal Images", Med Image Anal. Apr. 2014; 18(3): 555-566.

Yock, A.D. et al., "Forecasting longitudinal changes in oropharyngeal tumor morphology throughout the course of head and neck radiation therapy", Medical Physics, 2014 41(8): 119-129.

Zhang, P. et al., "Predictive Treatment Management: Incorporating a Predictive Tumor Response Model Into Robust Prospective Treatment Planning for Non-Small Cell Lung Cancer", International Journal of Radiation: Oncology Biology Physics, Pergamon Press, vol. 88, No. 2, Dec. 5, 2013, pp. 446-452.

Wang, P. et al., "A Mathematical Model of Tumor Volume Changes during Radiotherapy", The Scientific World Journal, vol. 27, No. 3, Jan. 1, 2013, pp. 1851-1855.

Unkelbach, J. et al., "Radiotherapy planning for glioblastoma based on a tumor growth model: improving target volume delineation", Physics in Medicine and Biology, Institute of Physics Publishing, Bristol GB, vol. 59, No. 3, Jan. 20, 2014, pp. 747-770.

Espinoza I.et al., "A voxel-based multiscale model to simulate the radiation response of hypoxic tumors", Medical Physics, AIP, Melville, NY, vol. 42, No. 1, Jan. 1, 1901, pp. 90-102.

ADAPTIVE RADIATION THERAPY PLANNING

CROSS-REFERENCE TO PRIOR APPLICATIONS

This application is the U.S. National Phase application under 35 U.S.C. § 371 of International Application Serial No. PCT/EP2016/076764, filed on Nov. 7, 2016, which claims the benefit of European Patent Application No. 15196772.6, filed on Nov. 27, 2015. This application is hereby incorporated by reference herein.

FIELD OF THE INVENTION

The invention generally relates to a planning of an external beam radiation therapy treatment of a patient. More specifically, the invention relates to a system, a method and a computer program for generating a radiotherapy treatment plan for a patient.

BACKGROUND OF THE INVENTION

In external beam radiation therapy, ionizing radiation is applied to target structures, such as tumors, within patients' bodies in order to control growth of or kill cancer cells. The radiation treatment is usually delivered in plural sessions, which are also referred to as treatment fractions in the art. In more advanced types of radiation therapy, such as so called intensity-modulated radiation therapy (IMRT), precise doses of radiation are applied to regions of the patient's body. In this respect, it is typically the goal to deliver a sufficiently high radiation dose to the target structure and to spare sensitive structures, such as organs, in the vicinity of the target structure as far as possible.

The treatment parameters for delivering the radiation and controlling the radiation treatment device are defined in a treatment plan, which is generated in a planning system. In particular, a so-called inverse planning procedure may be carried out by means of the planning system. In such a procedure, the target structure and the surrounding structures to be spared are identified and treatment goals are specified. Such treatment goals include objectives which may specify requirements for the radiation dose delivered to certain regions of the patient, which should be fulfilled, and/or constraints for the radiation doses delivered to certain regions, which must be fulfilled. Then, an optimization process is carried out to find the treatment plan which fulfills the specified treatment goals. This optimization process is usually an operator-guided procedure in which an operator (e.g. a physician) reviews the dose distribution resulting from the treatment plan in several steps and makes changes to the treatment goals in order to find the optimal dose distribution.

Such an inverse planning procedure is normally carried out on the basis of a stationary delineation of the target structure, which does not change during the radiation treatment. However, the delineation of target structure does usually change during the radiation treatment. So, a tumor changes due to its natural progression, which normally results in a growth of the tumor, and, most notably, due to the effects of the radiation therapy, which result in a (net) shrinkage of the tumor. More specifically, already the delivery of a high-dose one treatment fraction of a hypo-fractioned regime (i.e. a radiation therapy treatment delivered in a smaller number of fractions), the radiation therapy typically reduces the number of active tumor cells by a factor of 2, and near the end of the radiation treatment only a small number of active tumor cells typically remains.

If the original treatment plan generated on the basis of the (stationary) delineation of the tumor or target structure is used after shrinkage of the target structure, there is a high risk to affect healthy tissue by applying a high radiation dose to such tissue. This can be avoided in so-called adaptive radiation therapy. In accordance with this approach images of the target structure are captured during the course of the radiation therapy (particularly between certain treatment fractions) in order to determine the changed delineation of the target structure. Then, a re-planning procedure is carried out to adapt the treatment plan to the changed delineation of the target structure.

One drawback of such an adaptive radiation therapy is an increased clinical workload associated with the re-planning procedure, which is usually also made in an operator-guided procedure similar to the generation of the original treatment plan. This can even lead to delays in the delivery of the radiation treatment, which can compromise the outcome of the radiation therapy, since the maximum impact of the therapy is only achieved when it is delivered sufficiently quickly so that a repopulation of tumor cells is avoided.

WO 2010/094777 discloses a system for generating treatment plans for irradiating a patient's treatment volume. In the system, a plurality of different treatment plans is generated on the basis of deformation information regarding anticipated changes of the treatment volume over time. In one embodiment, the deformation information is obtained using calculations regarding physical changes of the treatment volume based upon elasticity information objects within the treatment volume. Using such deformation information a plurality of modified images is generated, and for each modified image, a treatment plan is generated. In order to deliver the treatment, the system selects a treatment plan which corresponds to the modified image that best matches to the patient data at the time of the treatment.

SUMMARY OF THE INVENTION

It is an object of the invention to allow for a more efficient generation of a treatment plan for a radiotherapy treatment, which takes into account changes of the delineation of the target structure during the radiotherapy treatment.

According to a first aspect, the invention suggests a system for generating a radiotherapy treatment plan for treating a target structure within a patient body, the treatment plan comprising parameters for controlling a delivery of radiation to the target structure. The system comprises (i) a modeling unit configured to determine a series of estimates of a delineation of the target structure for consecutive points of time during the radiation therapy treatment on the basis of a model quantifying changes of the delineation with time, and (ii) a planning unit configured to determine the treatment plan on the basis of the series of estimates of the delineation of the target structure.

By generating the treatment plan on the basis of the series of estimates of the delineation of the target structure, a treatment plan taking account of changes of the delineation of the target structure can already be determined in the initial planning phase prior to the delivery of the treatment and it is no longer necessary to adapted the treatment to such changes during the radiation treatment. Thus, the treatment plan can be generated more efficiently. In particular, the clinical workload for generating the treatment plan can be reduced and delays resulting from a re-planning during the treatment can be avoided.

For determining the estimates of the delineation of the target structure, the modeling unit preferably also receives a reference image of the target structure, and it preferably determines the series of estimates of the delineation on the basis of a reference image. In particular, the modeling unit may estimate changes of the delineation of the target structure starting from a delineation as shown in the reference image. Preferably, the reference is image is a three-dimensional image of the target structure.

In one embodiment of the invention, the estimate of the delineation for a point of time is determined on the basis of a radiation dose to be applied to the target structure prior to the point in time in accordance with the treatment plan. Hereby, it is possible to take changes of the delineation of the target structure into account, which result from the application of radiation to the target structure during the radiotherapy treatment. Such changes usually involve shrinkage of the target structure in the course of the treatment, and this embodiment particularly allows for adapting the treatment plan to the changes in the volume of the target structure in later phases of the radiotherapy treatment.

Prior to the radiotherapy treatment or during the radiotherapy treatment, additional treatments, such as a chemotherapy treatment, may be applied to the target structure. In this regard, one embodiment of the invention provides that the estimate of the delineation for a point in time is determined on the basis of expected effects of one or more treatments applied to the target structure in addition to the radiation treatment prior to the point in time. Hereby, it is possible to also consider changes of the delineation of the target structure resulting from additional treatment in the generation of the treatment plan. When such an additional treatment is applied to the target structure prior to the radiotherapy treatment, it is particularly possible to generate an adapted treatment plan already before the application of the additional treatment so that scheduling of the planning procedure is simplified. When the additional treatment is applied during the radiotherapy treatment, e.g. between two treatment fractions, delays resulting from an adaptation of the treatment plan during the treatment can be avoided.

Moreover, as said above, the delineation of the target structure does usually also change due to the natural progression, particularly due to cell diffusion and/or proliferation. In this regard, one embodiment of the invention provides that the estimate of the delineation for a point in time is determined on the basis of expected changes of the target structure, which are independent of external interventions. In particular, the estimate may be determined on the basis of an expected diffusion and/or proliferation of tissue cells. In addition or as an alternative, changes of structures surrounding the target structure may be considered in order to determine the estimate. In such a way, the accuracy of the estimate of the delineation for the point in time can be further improved.

In a further embodiment, the radiation is delivered to the target structure in a plurality of successive treatment fractions and the points of time correspond to at least some of the treatment fractions. In particular, the points in time may correspond to one selected point in time during each relevant treatment fraction, where the points in time during the relevant treatment fractions can, in principle, be selected arbitrarily. According to one example, the points in time may correspond to the scheduled start times of the relevant treatment fractions.

Moreover, the estimates of the delineation of the target structure determined on the basis of the model may deviate from the actual delineation for the points in time, e.g. because the model does not describe the changes of the delineation entirely accurately and/or due to incorrect input parameters used for the model calculation.

In one embodiment, the modeling unit is therefore configured to estimate a plurality of series of estimates of the delineation in accordance with different changes of the delineation with time, and the planning unit is configured to determine a plurality of treatment plans including one treatment plan for each series of estimates of the delineation.

In a related embodiment, the system further comprises an imaging unit for capturing an image of the target structure in connection with the application of a treatment fraction to the target structure and a monitoring unit configured for selecting a treatment plan from the plurality of treatment plans on the basis of the delineation of the target structure as shown in the image. The image may particularly be a three-dimensional image.

These embodiments allow for generating a collection of the treatment plans prior to the delivery of the radiotherapy treatment, which includes treatment plans for different series of estimates of the delineation of the target structure. If it is determined during the delivery of the radiation treatment that the actual delineation of the target structure deviates from one of the estimate, it is possible to change to another treatment plan generated on the basis of estimate which better matches the actual delineation. Thus, it is particularly not necessary to re-generate a treatment plan during the radiotherapy treatment in case of deviations between the actual delineation of the target structure and the model-based estimate.

In a further related embodiment of the invention, monitoring unit is configured to determine a value of at least one parameter of the delineation of the target structure as shown in the image and to select the treatment plan assigned to a delineation having a value of the least one parameter which most closely matches the determined value. The parameter may correspond to a volume of the target structure and/or a diameter of the target structure, particularly to a maximum diameter of the target structure. In a further embodiment, the parameter is calculated on the basis of a distance between landmark points positioned on the delineation and a predetermined point. The predetermined point may particularly correspond to an estimated center of the target structure. Likewise, other parameters may be used.

Moreover, one embodiment of the invention includes that the monitoring unit is configured to compare a value of at least one parameter of the delineation of the target structure as shown in the image with a value of the parameter for a delineation of the target structure included the series of estimates of the delineation to which the currently selected treatment plan is assigned and the selection unit is further configured to select another treatment plan if a difference between the values of the parameter exceeds a predetermined threshold. It is an advantage of this embodiment that monitoring unit does not have to search for a better treatment plan each time an image of the target structure is captured. Rather, this search—which may involve some computational complexity—is only made in case of larger deviations between the estimate of the delineation of the target structure and the actual delineation as shown in the images.

According to a further aspect of the invention, a method for generating a radiotherapy treatment plan for treating a target structure within a patient body is suggested, the treatment plan comprising parameters for controlling a delivery of radiation to the target structure. The method comprises:

determining a series of estimates of a delineation of the target structure for consecutive points of time during the radiation therapy treatment on the basis of a model quantifying changes of the delineation with time, and determining the treatment plan on the basis of the series of estimates of the delineation of the target structure.

According to a further aspect, the invention suggests a computer program executable in a processing unit of a system for generating a radiotherapy treatment plan for treating a target structure within a patient body, the treatment plan comprising parameters for controlling a delivery of radiation to the target structure. The computer program comprises program code means for causing the processing unit to carry out the aforementioned method. It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
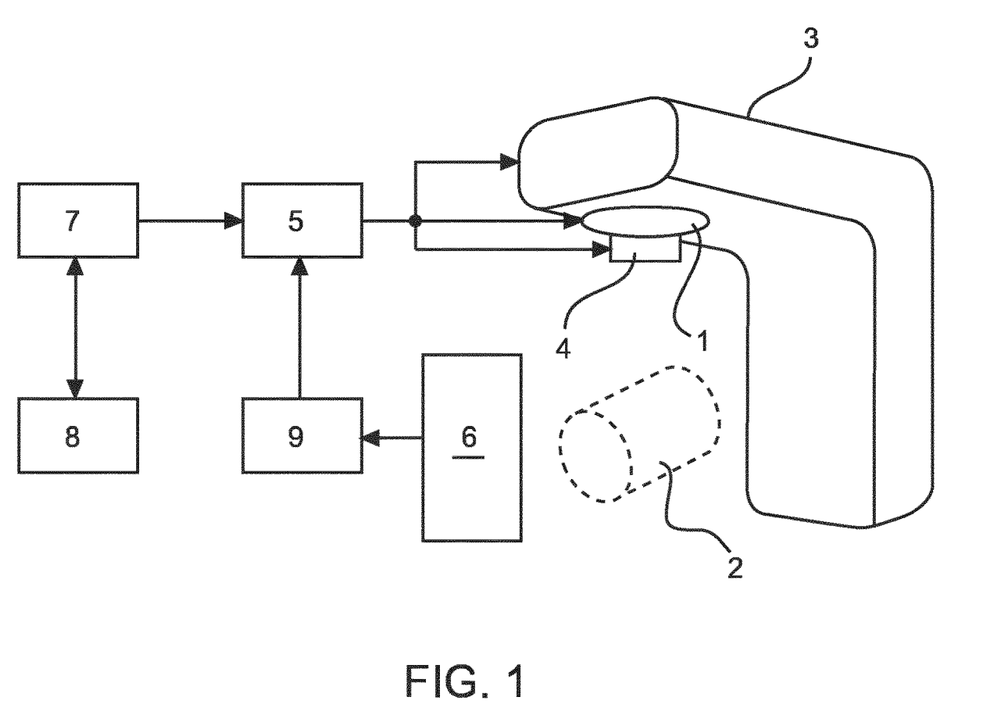
FIG. 1 schematically and exemplarily shows a radiation therapy system including a planning for generating a treatment plan, FIG. 2 schematically and exemplarily shows examples of tumor progression with time during and after radiation therapy, and FIG. 3 schematically and exemplarily shows two series of estimates of the delineation of the target structure and corresponding treatment plans and a series of actual delineations of the target structure.

FIG. 1 schematically and exemplarily illustrates an embodiment of a radiation therapy system for delivering radiation treatments to structures within a human or animal patient body. In particular, the system may be used to treat tumors within certain structures of the body. One example of such a structure is the lung as it is known that radiation therapy, particularly so-called stereotactic ablative radiation therapy (SBART), is especially suitable for treating lung cancer. It has been observed that particularly SBART treatment of lung tumors results in noticeable changes of the tumor volume in each treatment fraction. Such changes and similar changes in other radiotherapy treatments can be taken account of by adapting the treatment plan for the radiation therapy treatment as explained herein below.

In the illustrated embodiment, the radiation therapy system comprises a radiation source 1, which can be operated to emit ionizing radiation to be delivered to a tumor or another diseased target structure within a human or animal body positioned in a treatment zone 2 of the system on a support, which may be configured as a patient table. The relative position and orientation of the radiation source 1 with respect to the body or target structure can be varied over a certain range of positions and orientations. For this purpose, the radiation source 1 may be mounted on rotatable gantry 3 so that the radiation source 1 can be rotated around the treatment zone or body within a certain angular range, which may be 360° or less. In addition, the gantry 3 and/or the patient table may be movable back and forth in a direction parallel to the rotation axis of the gantry 3. Further, it may also be possible to rotate the patient table around an axis perpendicular to the rotation axis of the gantry 3.

The radiation source 1 may include an x-ray tube or a linear particle accelerator for producing one ionizing radiation beam; in further embodiments, the radiation system may produce several radiation beams in a similar way. The radiation source 1 is controllable in order to vary the intensity and/or energy of the radiation beam. Further, the radiation source 1 may be provided with a collimator 4 for shaping the radiation beam. The collimator 4 may particularly allow varying the radiation intensity across the radiation beam in a defined way. For this purpose, the collimator 4 may be configured as a so-called multi-leaf collimator. During delivery of the radiation treatment, the configuration of the collimator 4 is usually changed based on the treatment plan so that the radiation beam is delivered with a time-varying shape.

In one implementation, the radiation treatment is delivered in accordance with successive so-called segments, where each segment corresponds to a certain collimator configuration or beam shape and to certain (emitted) radiation dose, which may be specified in monitor units (MU). In between two segments, the collimator configuration is changed from the configuration of the first of the segments to the configuration of the second of the segments. During this period, the radiation beam may be turned off (this is usually also referred to as step-and-shoot approach). Likewise, it is possible to continuously change the collimator configuration and/or the emitted dose in accordance with the segments without interrupting the radiation beam, as it is the case in volume modulated arc therapy (VMAT), for example.

For controlling the radiation source 1, the collimator 4 and the patient table (if moveable) during the treatment (particularly for controlling the modifiable parameters of the radiation source 1, the collimator 4 and the patient table), the system includes a control unit 5. During a radiation therapy treatment, the control unit 5 controls the relative position and orientation of the radiation source 1 and the body by positioning the gantry 3 and/or the patient table. Further, the control unit 5 controls the intensity and energy of the radiation beam and the radiation beam shape. Preferably, the control unit 5 is implemented in a processor unit including a microprocessor for executing a control program comprising the control routines carried out by the control unit 5.

In addition, the radiation therapy system preferably comprises an imaging unit 6 for capturing images of the structure to be treated within the patient body. In different embodiments, the imaging unit 6 may comprise an ultrasound device, a computed tomography (CT) device (particularly a cone-beam computed tomography (CBCT) device), a magnetic resonance imaging (MRI) device or a fluoroscopy imaging unit, for example. Such devices are known to a person skilled in the art as such and, thus, they are not described in greater detail herein. By means of such a device, the imaging unit 6 produces two-dimensional or three-dimensional images of the body region including the structure to be treated. The imaging unit 6 may be arranged in the vicinity of the treatment zone 2 so that images of the relevant body region can be captured when the patient is located in the treatment zone 2, particularly during the radiation treatment or when a fraction of the radiation treatment is prepared. For this purpose, the imaging unit 6 and the radiation source 1 may be integrated into one device, or the imaging unit 6 may be a separate and possibly movable device which is arranged in the vicinity of the treatment zone 2.

The radiation treatment of the structure within the body may be performed during a plurality of fractions, where the fractions may be delivered to the structure on consecutive days or in another cycle. In order to deliver one fraction to the structure within the body, the body is positioned in the treatment zone 2 of the radiation therapy system at a defined position relative to the radiation source 1. Upon having positioned the body in treatment zone, the control unit 5 controls the delivery of radiation to the structure to be treated. In so doing, the control unit 5 aligns the radiation source 1 and controls the further parameters of the radiation source 1 and the collimator 4 in accordance with a treatment plan stored in the control unit 5 for the treatment of the specific patient.

The treatment plan defines the irradiation parameters for the radiation treatment of the structure. These parameters include the alignment of the radiation source 1 relative to the target region within the patient body, the collimator configurations to be used during the treatment and the radiation intensities.

For generating the treatment plan, the radiation therapy system comprises a planning unit 7. The planning unit 7 may be configured as a computer device, such as, for example a personal computer, which executes a treatment planning software for generating treatment plans which are then used by the control unit 5 for controlling the execution of the treatment fractions. In one embodiment, the planning unit 7 may be located in the vicinity of the control unit 5 and may be directly connected to the control unit 5, where the treatment plan may be transmitted from the planning unit 5 to the control unit 4 via this connection. In further embodiments, the planning unit 7 may be connected to the control unit 5 through one or more data networks, and the treatment plan may be transmitted via the network connection. Alternatively, the planning unit 7 may store the treatment plan in a suitable data recording means, and this data recording means may be transported to the control unit 5 which may then read the treatment plan from the data recording means. In the latter embodiments, the planning unit 7 may also be located remote from the control unit 5.

In the planning unit 7, the treatment plan may be generated using an inverse planning procedure. In such procedure, an operator of the planning unit 7, which may be a physician, specifies treatment goals, and the planning unit 7 produces a treatment plan that fulfills the treatment goals. The treatment goals particularly includes the objective that a certain radiation dose specified by the operator of the planning unit 7 is delivered to the target structure during the treatment fractions of the radiation therapy treatment. Further treatment goals may additionally relate to certain critical body regions, such as organs, which are located in the vicinity of the target structure and which are also referred to as structures at a risk hearing. In accordance with the treatment goals, these structures at risk are to receive no radiation or a lower radiation does than the target structure during the radiation therapy in order to prevent radiation-induced damages of the structures at risk.

The treatment goals particularly specify the delineations or volume of the target structure and the structures at risk, and specifications for the radiation dose to be delivered to the target structure and the structure at risk. On the basis of these input data, the planning unit may generate the treatment plan in accordance with an automatic procedure. As an alternative, the treatment plan may be generated in an iterative user-guided process. In each step of this process, the planning unit 7 may estimate a treatment plan on the basis of the treatment goals and may estimate a dose distribution resulting from the treatment plan. Then, the operator of the planning unit 7 may review the dose distribution and may change the treatment goals in case he/she is not satisfied with the dose distribution. In this manner, the treatment plan may be generated in a sequence of iterative steps.

The delineations of the target structure and the structures at risk are determined on the basis of a preferably three-dimensional reference image of the target structure and its surrounding. The reference image may be captured using the imaging unit 6 of the radiation therapy system, or the reference image may be captured using another imaging unit. In the reference image, a pattern recognition algorithm may automatically identify the target structure and the structures at risk and the boundaries or delineations of these structures. As an alternative, the target structure and the structures at risk may be manually delineated by the operator of the planning unit 7, or the delineations of the target structure and the structures at risk may be determined in a semi-automatic procedure, in which a pattern recognition algorithm automatically suggests the structures and their boundaries and in which the operator of the planning unit 7 can make manual changes to the automatically identified delineations.

In conventional inverse planning procedures, the delineation of the target structure (and of the structures at risk) is considered to be stationary and the treatment plan is generated on the basis of the assumption that the delineations of the target structure do not change until the end of the radiation therapy treatment. However, this assumption is often not correct since the delineation of the target structure usually changes within typical time periods of the treatment, which maybe several days or weeks. In particular, the volume of a tumor changes due to natural processes (i.e. independent of external interventions such as medical treatments), such as proliferation and diffusion of tumor cells. These processes usually result in a growth of the tumor. Further, the volume of the tumor changes due to external interventions. These interventions include the radiation therapy treatment and may also include further interventions, such as, for example, a chemotherapy treatment preceding the radiation therapy treatment. Such external interventions result in shrinkage of the tumor.

In order to efficiently account for such changes of the delineation of the target structure during the radiation therapy treatment, the radiation therapy system is capable of estimating the changes on the basis of a model calculation and to generate one or more treatment plans based on a dynamic delineation of the target structure that changes during the radiation therapy treatment. For this purpose, the radiation therapy system particularly includes a modeling unit 8 which is configured to perform model calculations of the changes of the delineation of the target structure. The modeling unit 8 may be coupled to the planning unit 7 and may be configured as a software program module which is executed on the same computer device as the planning unit 7. As an alternative, the modeling unit 8 may also be implemented in a separate computer device coupled to the planning unit 7.

The modeling unit 8 calculates estimates for the delineation of the target structure for a series of consecutive points in time during the radiation treatment of the target structure. In one embodiment, the points in time correspond to the treatment fractions as will also be assumed herein below. More specifically, an estimate may be calculated for one point in time of each treatment fraction. However, this point in time can be arbitrarily selected since any changes of the volume of the target structure during one treatment fraction are usually small.

In the calculation of the estimates of the delineation of the target structure, the modeling unit 8 preferably takes "natural" changes of the delineation into account (i.e. changes which area independent of external treatment options). Further, the modeling unit 8 is configured to calculate the estimate of the delineation of the target structure for one treatment fraction on the basis of the radiation dose delivered to the target structure in the preceding treatment fractions (if any). In addition, changes may be taken into account, which result from other treatments of the target structure between the capturing of the reference image and the radiation treatment. An example of such an additional treatment is a chemotherapy applied to the patient prior to the radiation therapy. Thus, in addition to the natural changes of the delineation of the target structure (which usually result in a tumor growth), changes of the target structure resulting from the application of external treatment options (which usually result are taken into consideration when generating the treatment plan on the basis of the estimated delineations of the target structure.

Figure 2:
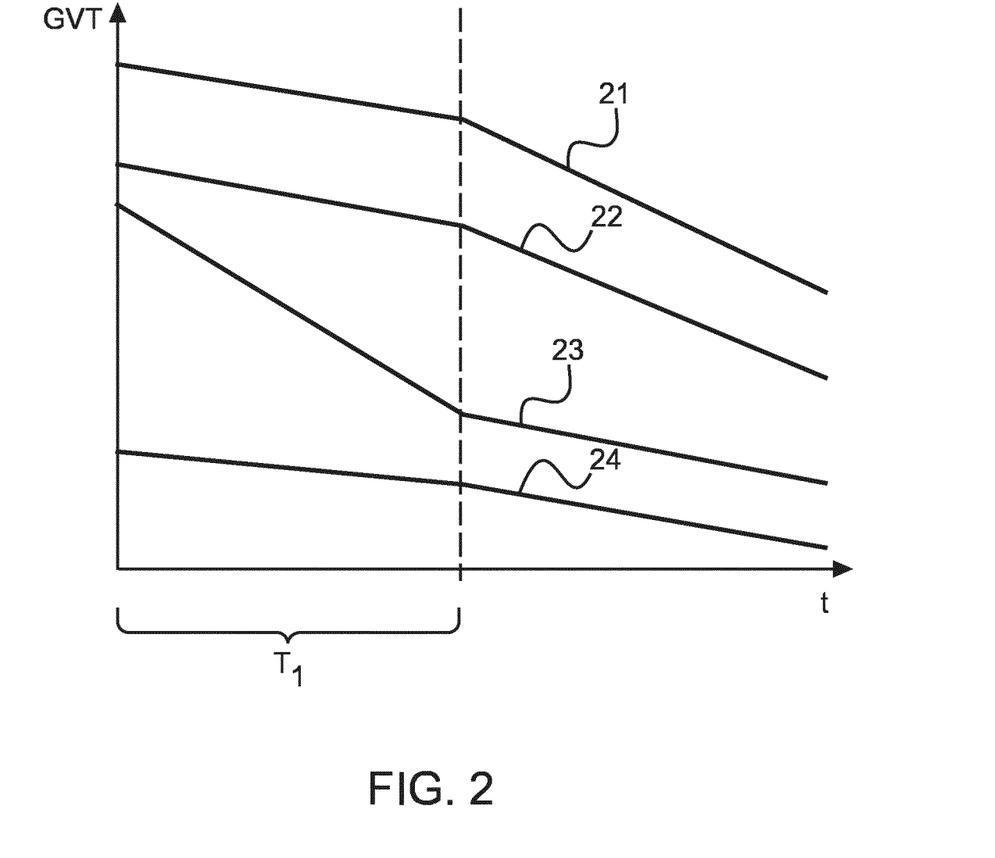

In FIG. 2 typical changes of tumor volumes GTV with time t are schematically and exemplarily illustrated. The figure includes curves 21-24, each showing the changes of a tumor volume during a multi-fraction radiotherapy treatment (time period $T_1$) and after completion of the radiation therapy.

In order to calculate the estimates of the delineation of the target structure, the modeling unit 8 uses a tumor progression model. Such models are known to the person skilled in the art as such and, in principle, any known tumor progression model may be applied in the modeling unit 8.

In one embodiment, a tumor progression model is used in which the natural changes of the target structure are estimated independent of the changes resulting from the external interventions and in which the net changes of the delineation of the target structure are determined as the sum of the natural changes and the changes resulting from the external interventions.

In view of the natural changes of the delineation of the target structure, it has been found that tumors change due to the proliferation of tumor cells and due to the diffusion of tumor cells. In order to model the diffusion of the tumor cells, it can be assumed that the flux due to the diffusion is proportional to the gradient of tumor cell density. With respect to cell proliferation a linear relationship in the tumor cell density may be assumed, resulting in an exponential growth of the tumor. This usually provides an accurate description of tumor growth on time scales that are short in comparison to the expectancy after initial tumor development. Under these assumptions, the tumor cell density changes according to $$\frac{\partial n}{\partial t} = \nabla \cdot (D\nabla n) + \mu n(1 - n/n_0) \qquad (1)$$

where n denotes the tumor cell density, D denotes the diffusivity of the tumor cells, μ denotes the cell proliferation rate, $n_0$ denotes a reference tumor cell density and t is a time variable. On the basis of this equation, the change of the tumor cell density within a region of interest can be calculated, and based on the result of this calculation, the changes of the delineation of the target structure resulting from the natural development can be determined.

The effects of radiation therapy and other external interventions may be modeled on the basis of an estimated probability that a tumor cell survives the intervention or on the basis of an estimated proportion of the tumor cells surviving the external intervention. With respect to radiation therapy, these parameters depend on the radiation dose applied to the tumor and also on how the body of the patient biologically receives the applied radiation. Therefore, the parameters may be calculated on the basis of the radiation dose applied during the radiation treatment (before the point of time for which the calculation is made) and on the basis of the so-called biologically effective dose (BED), which indicates quantitatively the biological effect of the radiotherapy treatment. The net estimated change of the tumor cell density resulting from external interventions may be added to the right side of equation (1) so that the overall change of tumor cell density is given by the model equation $$\frac{\partial n}{\partial t} = \nabla \cdot (D\nabla n) + \mu n(1 - n/n_0) + f(n, \vec{x}, t) \qquad (2)$$

where the function f incorporates the net decay (or growth) of the tumor cell density imposed by external interventions. As indicated in equation (2), this function generally depends on time t, on location $\vec{x}$ and on the tumor cell density n. On this of this equation or a similar equation, changes of the tumor cell density can be calculated and from these changes, the changes of the volume or the delineation of the tumor can be determined.

The parameters of the model may be measured or estimated for the specific patient or they may be derived from previous patient data. In particular, tumor progression may be monitored for a larger number of patients and the model may be fitted to the observed tumor progressions in order to estimate the parameters. In such a way the model may be "trained" on the basis of previous patient data.

With respect to brain tumors, a similar model for tumor progression is also explained in S. Nawrocki, B. Zubik-Kowal, "Clinical study and numerical simulation of brain cancer dynamics under radiotherapy", Commun Nonlinear Sci Numer Simulat 22 (2015) 564-573 (doi: 10.1016/j.cnsns.2014.08.001). This publication describes one specific model calculation, which may also be performed in the modeling unit 8 in order to calculate estimates of the delineation of the target structure. Further tumor progression models, which are also suitable to take into account the effects of a chemotherapy treatment prior to the radiotherapy treatment and which may be applied in the modeling unit 8 are described in G. G. Powathil et al., "Towards Predicting the Response of a Solid Tumour to Chemotherapy and Radiotherapy Treatments: Clinical Insights from a Computational Model", PLoS Comput Biol 9(7): e1003120 (doi: 10.1371/journal.pcbi.1003120), and in Y. Liu et al., "Patient Specific Tumor Growth Prediction Using Multimodal Images", Med Image Anal. 2014 April; 18(3): 555-566 (doi: 10.1016/j.media.2014.02.005). further suitable tumor progression models are disclosed in A. D. Yock et al., "Forecasting longitudinal changes in oropharyngeal tumor morphology throughout the course of head and neck radiation therapy", Medical Physics, 2014 41(8):119-129. The models used in this publication forecasts longitudinal trends in changing tumor morphology. In particular, the modeling unit 8 may use the linear model described in this publication.

Using a suitable tumor progression model, such as, for example, one of the aforementioned tumor progression models, the modeling unit 8 calculates the estimates for the delineation of the target structures for the points in time during the radiotherapy treatment. The calculation is made starting from the delineation of the target structure as shown in the reference image. Moreover, patient-specific biological parameters, which are used in the model calculation, such as, for example, the tumor cell diffusivity, the cell proliferation rate and the parameters specifying how the patient body receives radiation, may be estimated on the basis of suitable medical examinations of the patient and/or on the basis of general medical data. Further, the modeling unit 8 calculates the estimates of the delineation of the target structure for a certain treatment fraction on the basis of the radiation doses to be delivered to the target structure prior to the treatment fraction (i.e. in preceding treatment fractions).

In addition to the changes of the delineation of the target structure, also the delineation of the structures at risk in the vicinity of the target structure change. Such changes result from the volume change of the target structure and may also result from inherent dynamics of the structures at risk. In this regard, the modeling unit 8 may also determine estimates for the delineations of structures at risk and may consider (inherent) changes of the structures at risk when estimating the delineations of the target structure. The estimates for the structures at risk may particularly be determined on the basis of a priori knowledge about the response of the structures at risk to changes of the volume of the target structure or tumor within a certain body region, and, in addition, the modeling unit 8 may also use a model for the inherent dynamics of the structures at risk.

The dynamics of the structures at risk may be modeled on the basis of the changes of the target structure. So, a reduced volume of the target structure usually leads to a smaller compression of the structure at risk and, as a result, the structure at risk may move and/or its volume may change. In order to estimate such movements and/or volume changes patient data may be used. In particular, changes of both the target structure and the surrounding structures at risk may be monitored for a number of patients and the changes may be statistically evaluated in order to create a model of the changes of the structures at risk with the changes of the target structure. Using such a model, the modeling unit 8 may estimate changes of the delineations of the structures at risk on the basis of the estimated changes of the target structure.

In the following description of the planning process, the estimates of delineations of structures at risk are not always explicitly referred to. Rather, it is only referred to the estimates of the delineation of the target structure. However, it is to be understood that each single estimate of the delineation of the target structure can be accompanied by a corresponding estimate of the delineations of structures at risk and that also these estimates are used in the generation of the treatment plan.

On the basis of the estimates of the delineation of the target structure (and, as said above, also on the basis of the estimates of structure at risk, if present), the planning unit 7 generates one or more treatment plans. In this process, treatment parameters and estimates of the delineation of the target structure may be exchanged between the planning unit 7 and the modeling unit 8. In particular, the treatment plan(s) may be generated in an iterative process in which the planning unit 7 determines treatment parameters for certain treatment fractions. On the basis of these treatment parameters, particularly on the basis of the resulting radiation dose applied the target structure, the modeling unit 8 may then determine an estimate of the delineation of the target structure for one or more subsequent treatment fractions, and estimate may be used by the planning unit 7 in order to determine treatment parameters for the subsequent treatment fraction(s). In such a way, the treatment parameters for all treatment fractions may be determined on the basis of the estimates of the delineation of the target structure.

In one related embodiment, the planning unit 7 may calculate a first treatment plan on the basis of the reference image in a conventional inverse planning procedure (i.e. without considering changes of the delineation of the target structure). In this treatment plan, the treatment parameters for the first treatment fraction will be maintained in the final treatment plan, while the treatment parameters for the other treatment fractions may be re-calculated on the basis of the estimates of the delineation of the target structure determined in the modeling unit 8. More specifically, the modeling unit 8 may calculate an estimate of the delineation of the target structure for the second treatment fraction on the basis of the radiation delivered to the target structure during the first treatment fraction in accordance with the treatment plan. On the basis of this estimate, the planning unit 7 may then re-calculate the treatment parameters for the second and the subsequent treatment fractions in an inverse planning procedure. From the resulting treatment plan, the treatment parameters are maintained for the second treatment fraction The treatment parameters for the third and the subsequent treatment fractions may then be determined in a similar way as the treatment parameters for the second treatment fraction on the basis of corresponding estimates of the delineation of the target structure determined in the modeling unit 8.

The aforementioned approach does in principle correspond to a conventional adaptive treatment planning. It differs from such conventional adaptive treatment planning in that the adaptations of the treatment plan are not made on the basis of images of the target structure captured during the radiation treatment but on the basis of the estimates of the delineation of the target structure determined in the modeling unit 8 in the planning phase prior to the treatment.

In the way explained above, the planning unit 7 can generate a treatment plan for the radiotherapy treatment of a patient which takes into account the estimates changes of the delineation of the target structure. This treatment plan may be provided to the control unit 5 of the radiation therapy system, and the control unit 5 may control the delivery of the radiotherapy treatment to the patient using the treatment plan.

As explained above, the estimates of the delineation of the target structure as determined in the modeling unit 8 depend on input parameters relating to biological characteristics of the patient. In some cases, these parameters cannot be accurately determined for a patient. In addition, the model calculation itself does usually not consider all relevant factors influencing the changes of the delineation of the target structure. In particular for these reasons, the actual changes of the delineation of the target structure will in some cases differ from the estimates calculated in the modeling unit 8.

In view of such deviations between the estimates of the delineation of the target structure and the actual delineation, images of the target structure may be captured using the imaging unit 6. In particular, an image may be captured in the preparation of each or some of the treatment fractions. However, it is likewise possible that images of the target structure are acquired during the delivery of the radiotherapy treatment. The images of the target structure are provided to a monitoring unit 9 of the radiation therapy system, which may be integrated into the control unit 5, for example, and which also obtains from the modeling unit 8 the estimates of the delineation of the target structure or the assigned parameters as explained below. The monitoring unit 9 compares each image with the corresponding estimate of the delineation of the target structure, i.e. the estimate for the treatment fraction for which the image is captured using the imaging unit 6. On the basis of the comparison, the monitoring unit 8 determines detects possible deviations between the estimate of the delineation of the target structure and the actual delineation as show in the image. For this purpose, the comparison may be made on the basis of any suitable criterion. In particular, the monitoring unit 9 may determine values of one or more parameters of the delineation of the target structure and compare them with corresponding parameter values of the estimate.

Examples of such parameters are the maximum diameter of the target structure and the volume of the target structure. In a further embodiment, corresponding landmarks are assigned to the target structure as shown in the image and to the estimate of the target structure and the positions of the landmark patterns are compared with each other. For this purpose, a similarity parameter may be calculated for the landmark pattern for the target structure as shown in the image and this similarity measure may be compared with the corresponding similarity parameter determined for the estimated delineation of the target structure. In one implementation of this procedure, the target structure and preferably also the structures at risk are provided with surface landmarks in the three-dimensional captured image of the relevant body region. Further, this image is registered to the corresponding estimated picture of the target structure and structures at risk on the basis of which the treatment plan has been generated. In this registration process, the image and the included landmark pattern is deformed and the deformed landmark pattern is used as the landmark pattern for the estimated delineation of the target structure and possibly of the structures at risk. Then, a feature vector may be calculated on the basis of the landmark pattern in the image and the landmark pattern for the estimate, respectively. For the target structure and optionally for each structure at risk, the feature vector may include for each landmark the distance between the landmark and the center of a structure. Moreover, the feature vector may include the aforementioned parameters for the target structure and each relevant structure at risk. The similarity parameter may then be computed as a function of the components of the feature vector, which may include different weights for the components relating to the target structure and the components relating to different structures at risk.

When the monitoring unit 9 determines that the difference between the similarity parameters for the actual delineation and the estimate exceeds one or more predetermined thresholds, the treatment plan is preferably no longer used for controlling the delivery of the radiation therapy treatment to the patient. In one embodiment, the planning unit 7 may generate a new treatment plan in the way described above in this case, where the image may be used as the reference image for the generation of the new treatment plan and where the treatment goals (particularly specifying the radiation dose to be delivered to the target structure) are adapted to the preceding delivery of the radiation treatment.

In a further embodiment, the modeling unit 8 calculates several series of estimates of the delineation of the target structure and for each series a treatment plan is generated in the planning unit 7 during the planning phase prior to the initiation of the radiotherapy treatment. In this embodiment, the different series of estimates of the delineation may be calculated in the modeling unit 8 on the basis of different values for the biological parameters of the patient, where each series may be calculated on the basis of one parameter set including a particular value for each relevant parameter. One set of parameter values may correspond to the values of the relevant parameters measured for the patient and/or estimated on the basis of measurements. Other sets of parameter values may correspond to values in the vicinity of the values derived from the measurements. In addition or as an alternative, the different series of estimates of the delineation of the target structure may be calculated using different models. The models may differ in the values of certain model parameters, or structurally different models may be used.

For each series of estimates of the delineation of the target structure, a treatment plan is generated on the basis of the estimates in a similar way described above. These treatment plans preferably provide for the delivery of the same overall radiation dose to the target structure. However, the treatment plans may particularly differ with respect to the radiation dose applied to the structures at risk.

Thus, the planning unit 7 generates a collection of treatment plans and each treatment plan is associated with one series of estimates of the delineation of the target structure. Then, the collection of treatment plans is provided to the control unit 5 and the series of estimates or the relevant parameter values for the estimates are provided to the monitoring unit 9. Then, the radiotherapy treatment of the patient may be started using one the treatment plans of the collection. For instance, this may be the treatment plan generated using the series of estimates calculated on the basis of measured parameter values, if the different series of estimates are generated using different sets of parameter values. In case parameter values are derived from patient data and/or structurally different models are used, the treatment may be started using the treatment plan generated using the series of estimates calculated on the basis of a model or parameter set which best describes the tumor progression for a larger number of patients. During the radiation treatment and/or in the process of preparing treatment fractions, the imaging unit 6 acquires images of the target structure, and the monitoring unit 9 compares the delineation of the target structure as shown in the images with the estimates of the delineation of the target structure associated with the selected treatment plan. This comparison may be made on the basis of one or more similarity parameters of the target structure as explained above. If the monitoring unit 9 determines that the difference(s) between the parameter values of the actual delineation and the estimate exceeds a predetermined threshold, the monitoring unit 9 accesses the series of estimates of the delineation of the target structure, which are associated with the other treatment plans of the collection of the treatment plans. From these series, the monitoring unit 9 selects the estimate of the delineation, which corresponds to the same treatment fraction as the acquired image and which has values of the relevant similarity parameters which have the smallest difference to the parameter values of the actual delineation. Further, the monitoring unit may check whether the already administered radiation dose correspond to the radiation dose that would have been administered in case the selected new treatment plan was used. If the difference between both doses is smaller than a threshold, the selected new treatment plan can successfully account for the changes of the target structure, and monitoring unit 9 may instruct the control unit 5 to switch to this treatment plan.

In a further embodiment, the monitoring unit 8 does also take into account estimates of delineations of structures at risk and actual delineations of these structures. These delineations may particularly be considered in the calculation of the similarity parameters, for example in the way described above. In this embodiment, the monitoring unit 8 determines the estimate of the delineation of the target structure and the accompanying estimates of delineations of structure at risk, which best match the captured image showing the target structure and the structure at risk in accordance with predefined matching criteria. In some cases, this may lead to a different selection than in case only the estimated and the actual delineation of the target structure are considered.

Upon having selected an estimate of the delineation of the target structure as described above, the monitoring unit 9 instructs the control unit 5 to use the treatment plan associated with the selected estimate for further controlling the radiation treatment of the patient. Upon this instruction, the control unit 5 activates the new treatment plan and uses this treatment plan for the further control of the radiation treatment. In so doing, the control unit 5 accesses the portions of the new treatment plan which correspond to the current treatment fraction and the subsequent treatment fractions.

In the further course of the radiation treatment, the monitoring unit 9 preferably continues to compare the actual delineations of the target structure (as shown in the images acquired by the imaging unit 9) and the estimate of the delineation associated with the activated treatment plan and instructs the control unit 5 to change to a new treatment plan, when it determines that deviation between the actual delineation and the estimate becomes too large.

Thus, in the aforementioned embodiment, it is particularly possible to correct inaccuracies of the model calculation of the delineation of the target structure by providing a collection of treatment plans associated with different series of estimates of the delineation of the target structure and by using the treatment plan associated with a series of estimates that best matches the actual delineation at a certain point in time.

Figure 3:
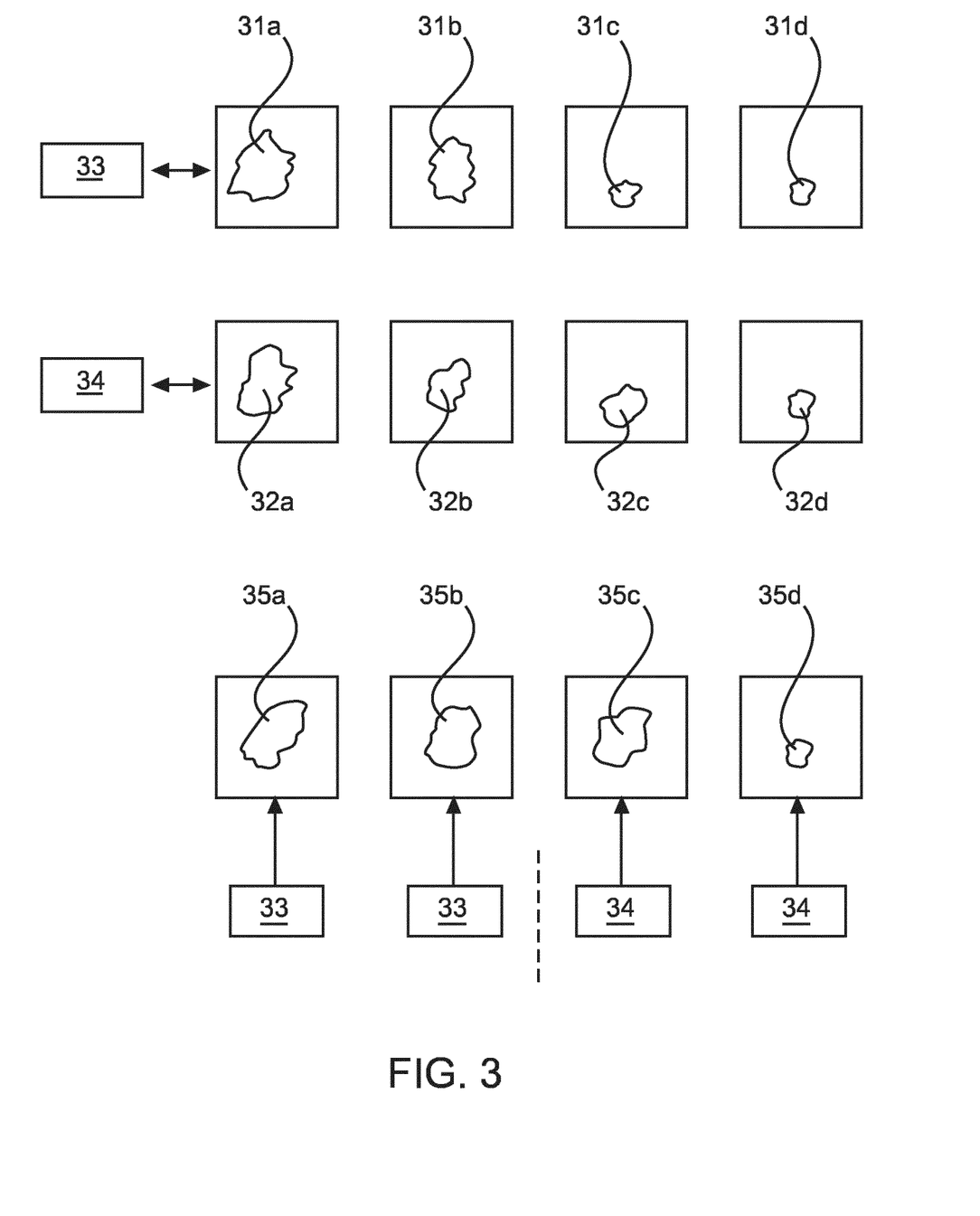

This is also exemplarily and schematically illustrated in FIG. 3. This figure schematically shows four estimates 31a-31d of the delineation of the target structure for different points in time which are included in a first series of estimates and four estimates 32a-32d of the delineation of the target structure for the same points in time included in a second series of estimates. The first series of estimates of the delineation of the target structure corresponds to a first treatment plan 33 and the second series corresponds to a second treatment plan 34. In addition, FIG. 3 shows actual delineations 35a-35d of the target structure as shown in images captured at the relevant points in time (which may correspond to treatment fractions as explained above).

In the situation exemplarily illustrated in FIG. 3, the first treatment plan 33 is used for controlling the radiotherapy treatment upon the first and second points in time. At the third point in time, the deviation between the corresponding estimate 31c of the delineation of the target structure (associated with the first treatment plan 33) and the actual delineation 25c of the target structure becomes larger, and the estimate 32c of the delineation of the target structure (associated with the second treatment plan 34) does better correspond to the actual delineation 35c of the target structure. Therefore, the first treatment plan 33 is no longer upon the third point in time. Rather, the radiation treatment is controlled in accordance with the second treatment plan 34 upon the third point in time.

In the embodiments explained above, treatment plans are generated which take account of changes of the volume of the target structure and the structure at risk. In addition, it also possible to take account of positions changes of the target structure and preferably also of the structures at risk. For this purpose, each of the aforementioned treatment plans may be replaced by a set of treatment plans, where each treatment plan of this set is generated for a different position of the target structure. If multiple series of estimates of the delineation of the target structure and corresponding collections of treatment plans are determined as explained above, one of such sets may be used for each treatment plan included in the collections. The different positions may correspond to grid points of a regular grid surrounding the actual position of the target structure in the reference image, for example.

In this embodiment, the monitoring unit 9 does may also determine the actual positions of the target structure and optionally of the structures and may select a new treatment plan, in case the actual position deviates from the position assumed when generating the currently used treatment plan. Particularly in case multiple series of estimates of the delineation of the target structure and corresponding collections of treatment plans are determined, the positions of the target structure and the structures at risk may also be considered when calculating the similarity parameters for the captured images and the estimates (including estimates for different positions in this embodiment). This may be done by including the center position of each relevant structure in the feature vector described above.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for generating a radiotherapy treatment plan for treating a target structure within a patient body, the treatment plan comprising parameters for controlling a delivery of radiation to the target structure, the system comprising:
   a modeling unit configured to determine a series of estimates of a delineation of the target structure for consecutive points of time during the radiation therapy treatment on the basis of a model quantifying changes of the delineation with time, and
   a planning unit configured to determine the treatment plan on the basis of the series of estimates of the delineation of the target structure, wherein the estimate of the delineation for a point of time is determined on the basis of a radiation dose to be applied to the target structure prior to the point in time in accordance with the treatment plan.

2. The system as defined in claim 1, wherein the modeling unit is configured to receive a reference image of the target structure and to determine the series of estimates of the delineation on the basis of a reference image.

3. The system as defined in claim 1, wherein the estimate of the delineation for a point in time is determined on the basis of expected effects of one or more treatments applied to the target structure in addition to the radiation treatment prior to the point in time.

4. The system as defined in claim 1, wherein the estimate of the delineation for a point in time is determined on the basis of expected changes of the target structure, which are independent of external interventions.

5. The system as defined in claim 1, wherein the radiation is delivered to the target structure in a plurality of successive treatment fractions and wherein the points of time correspond to at least some of the treatment fractions.

6. The system as defined in claim 1, wherein the modeling unit is configured to estimate a plurality of series of estimates of the delineation in accordance with different changes of the delineation with time, and wherein the planning unit is configured to determine a plurality of treatment plans including one treatment plan for each series of estimates of the delineation.

7. The system as defined in claim 6, further comprising an imaging unit for capturing an image of the target structure in connection with the application of a treatment fraction to the target structure and a monitoring unit configured for selecting a treatment plan from the plurality of treatment plans on the basis of the delineation of the target structure as shown in the image.

8. The system as defined in claim 7, wherein the image is a three-dimensional image.

9. The system as defined in claim 7, wherein the monitoring unit is configured to determine a value of at least one parameter of the delineation of the target structure as shown in the image and to select the treatment plan assigned to a delineation having a value of the least one parameter which most closely matches the determined value.

10. The system as defined in claim 7, wherein the monitoring unit is configured to compare a value of at least one parameter of the delineation of the target structure as shown in the image with a value of the parameter for a delineation of the target structure included the series of estimates of the delineation to which the currently selected treatment plan is assigned and wherein the monitoring unit is further configured to select another treatment plan if a difference between the values of the parameter exceeds a predetermined threshold.

11. The system as defined in claim 9, wherein the parameter corresponds to a volume of the target structure and/or a diameter of the target structure, particularly to a maximum diameter of the target structure.

12. The system as defined in claim 9, wherein the parameter is calculated on the basis of a distance between landmark points positioned on the delineation and a predetermined point, the predetermined point particularly corresponding to an estimated center of the target structure.

13. A method for generating a radiotherapy treatment plan for treating a target structure within a patient body, the treatment plan comprising parameters for controlling a delivery of radiation to the target structure, the method comprising:

determining a series of estimates of a delineation of the target structure for consecutive points of time during the radiation therapy treatment on the basis of a model quantifying changes of the delineation with time, and determining the treatment plan on the basis of the series of estimates of the delineation of the target structure, wherein the estimate of the delineation for a point of time is determined on the basis of a radiation dose to be applied to the target structure prior to the point in time in accordance with the treatment plan.

14. A computer program executable in a processing unit of a system for generating a radiotherapy treatment plan for treating a target structure within a patient body, the treatment plan comprising parameters for controlling a delivery of radiation to the target structure, the computer program comprising program code means for causing the processing unit to carry out a method as defined in claim 13.

* * * * *